United States Patent
Casset et al.

(10) Patent No.: US 11,559,240 B2
(45) Date of Patent: Jan. 24, 2023

(54) METHODS AND TOOLS TO MERGE MAPPING DATA ACQUIRED FROM MULTIPLE CATHETERS

(71) Applicant: ST. JUDE MEDICAL, CARDIOLOGY DIVISION, INC., St. Paul, MN (US)

(72) Inventors: Cyrille Casset, Saint Selve (FR); Jan Mangual, Rho (IT); Chunlan Jiang, Northridge, CA (US); Craig Markovitz, Mahtomedi, MN (US); Louis-Philippe Richer, Montreal Quebec (CA)

(73) Assignee: ST JUDE MEDICAL CARDIOLOGY DIVISION, INC, St Paul, MN (US)

( * ) Notice: Subject to any disclaimer, the term of this patent is extended or adjusted under 35 U.S.C. 154(b) by 121 days.

(21) Appl. No.: 17/012,926

(22) Filed: Sep. 4, 2020

(65) Prior Publication Data
US 2021/0068690 A1      Mar. 11, 2021

Related U.S. Application Data

(60) Provisional application No. 62/896,864, filed on Sep. 6, 2019.

(51) Int. Cl.
| A61B 5/339 | (2021.01) |
| A61B 5/00 | (2006.01) |
| A61B 5/30 | (2021.01) |
| A61B 5/287 | (2021.01) |

(52) U.S. Cl.
CPC ............. *A61B 5/339* (2021.01); *A61B 5/287* (2021.01); *A61B 5/30* (2021.01); *A61B 5/6852* (2013.01)

(58) Field of Classification Search
CPC ................... A61B 5/367; A61B 5/339; A61B 2018/00839
See application file for complete search history.

(56) References Cited

U.S. PATENT DOCUMENTS

| 7,263,397 | B2 | 8/2007 | Hauck et al. | |
| 8,463,368 | B2 * | 6/2013 | Harlev | A61B 5/35 600/509 |
| 9,955,889 | B2 * | 5/2018 | Urman | G16H 50/50 |
| 10,082,395 | B2 * | 9/2018 | Koyrakh | G01C 21/00 |
| 2014/0200467 | A1 * | 7/2014 | Strom | A61B 5/0044 600/300 |
| 2018/0014751 | A1 | 1/2018 | Hill et al. | |

\* cited by examiner

*Primary Examiner* — George R Evanisko
(74) *Attorney, Agent, or Firm* — Billion & Armitage (57) ABSTRACT

The present disclosure is directed to merging data acquired from differently configured catheters on a common map. In use, physical characteristics of catheters influence recorded electrical signals/responses such that differently configured catheters (e.g., different electrode sizes, shapes, materials, spacings, etc.) may record different responses to measurements taken at the same location in response to the same excitation signal. To allow merging of data from differently configured catheters in a common map, the present disclosure applies a corrective coefficient or transfer function to the recorded electrical signals of one or both catheters to counter-balance variable influences of catheter specific characteristics on recorded signals.

6 Claims, 8 Drawing Sheets

METHODS AND TOOLS TO MERGE MAPPING DATA ACQUIRED FROM MULTIPLE CATHETERS

CROSS-REFERENCE TO RELATED APPLICATION(S)

This application claims benefit of U.S. Provisional Application No. 62/896,864, filed on Sep. 6, 2020 and which application is incorporated herein by reference. A claim of priority is made.

FIELD

The present disclosure relates to electrical mapping of internal patient cavities such as cardiac cavities. More specifically, the present disclosure relates to merging mapping data acquired form two or more separate catheters.

BACKGROUND

A number of mapping and navigation options have been developed to enable electrical mapping of a patient's heart as well as navigation of an instrument, such as an electrode catheter, to a desired site for ablation or other treatment. For example, the EnSite Precision™ Cardiac Mapping System is a catheter navigation and mapping system capable of displaying the 3-dimensional (3-D) position of electrophysiology catheters, as well as displaying cardiac electrical activity as waveform traces and as dynamic 3-D isopotential maps of the cardiac chamber. The contoured surfaces of these 3-D maps are based on the anatomy of the patient's own cardiac chamber. The EnSite system and similar systems are generally based on the principle that when electrical current is applied across two surface electrodes, a voltage gradient is created along the axis between the electrodes. Although any suitable number of electrodes may be utilized, typically six surface electrodes are placed on the body of the patient and in three pairs: anterior to posterior, left to right lateral, and superior (neck) to inferior (left leg). The three electrode pairs form three orthogonal axes (X-Y-Z), with the patient's heart being at least generally at the center.

The noted six surface electrodes are connected to a mapping system, which alternately sends an electrical signal through each pair of surface electrodes to create a voltage gradient along each of the three axes, forming a transthoracic electrical field. Electrophysiology catheters may be connected to the mapping system and advanced to the patient's heart. As a catheter enters the transthoracic field, each catheter electrode senses voltage, timed to the creation of the gradient along each axis. Using the sensed voltages compared to the voltage gradient on all three axes, the mapping system calculates the three-dimensional position of each catheter electrode. The calculated position for the various electrodes may occur simultaneously and may repeat multiple times per second.

The mapping system may display the located electrodes as catheter bodies with real-time navigation. By tracking the position of the various catheters, the mapping system may provide non-fluoroscopic navigation, mapping, and creation of chamber models that are highly detailed and that have highly accurate geometries. In the latter regard, the physician typically sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired/required. In order to generate an accurate and highly detailed map of a patient's heart, an electrode catheter may be swept across various surfaces of the heart while obtaining data as described above.

BRIEF SUMMARY OF THE DISCLOSURE

Various arrangement herein provide systems, methods and/or non-transitory computer readable medium storing instructions (i.e., utilities) for use in adjusting responses of differently configured catheters to a common frame of reference, which allows merging data from the different catheters in a common map. In various arrangements, responses are acquired from a first catheter disposed in a three-dimensional space (e.g., patient heart). Such responses may include electrode responses to an electrical field applied to the three-dimensional space. Information from at least a portion of the responses from the first catheter are utilized to generate a map of a portion of the three-dimensional space (e.g., heart chamber). Responses are then acquired from a second catheter having a configuration (e.g., physical) that is different than the first catheter. The responses from the second catheter are adjusted. Once adjusted, the responses from the second catheter and the responses from the first catheter are scaled to a common frame of reference. Information from at least a portion of the adjusted second responses may then be incorporated into the map of the three-dimensional space to generate an updated map having information from the first and second catheters. An image of the updated map may then be output to a display.

In an arrangement, the responses of the second catheter are adjusted based on a corrective coefficient or transfer function. In one embodiment the transfer function is a magnifier that scales the responses (e.g., amplitudes) of the second catheter. In a specific embodiment, the magnifier is based on a ratio of magnitude of a response of the second catheter to the magnitude of a response of the first catheter or a reference catheter to a common signal under common conditions. The magnifier is typically specific to a given catheter and may be multiplied with subsequent responses of the catheter to scale its responses to another catheter. In an arrangement, the magnifier may scale the second catheter responses directly to the first catheter responses. In another arrangement, the responses of both the first and second catheters may be scaled to a reference catheter. In this latter arrangement, the reference catheter is the common frame of reference.

In another arrangement, the corrective coefficient or transfer function is based on two or more catheter characteristics. Such characteristics may include, without limitation, electrode size, electrode shape, electrode material and/or electrode spacing. The transfer function may be defined as a product of the ratios of two or more characteristics of the second catheter relative to the same characteristics of the first catheter or the reference catheter.

In a further arrangement, the corrective coefficient or transfer function may be selected based on a measured parameter. By way of example only, contact forces and/or impedances (to name a few) may be correlated between different catheters (e.g., a second catheter and a reference catheter). Upon measuring the parameter (e.g., by the second catheter) during use, a magnifier may be selected that will scale the measured parameter to what another catheter (e.g., reference catheter) would be measure for that parameter.

The foregoing and other aspects, features, details, utilities and advantages of the present disclosure will be apparent

DETAILED DESCRIPTION

Figure 1:
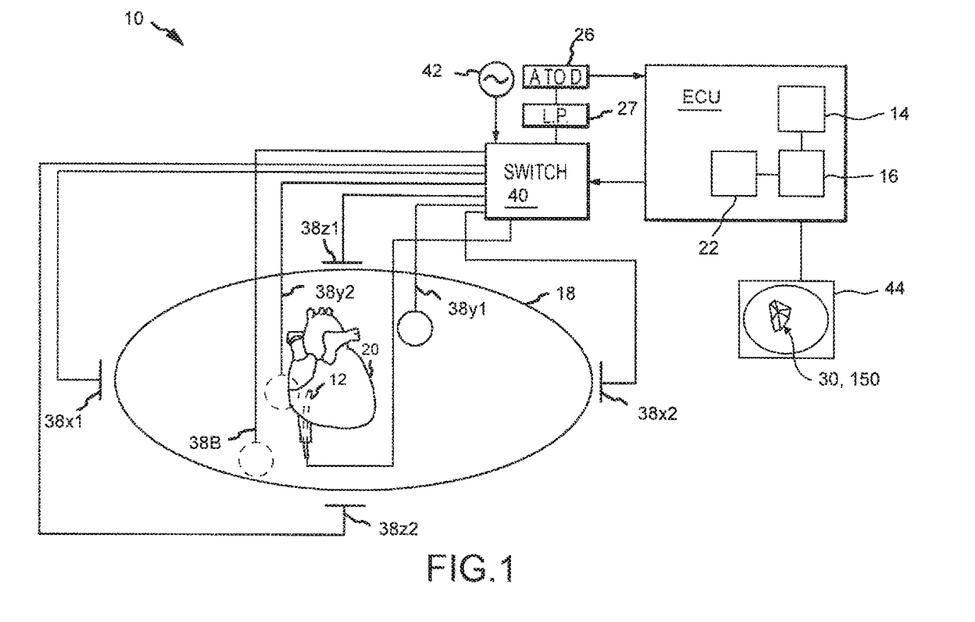
FIG. 1 is a diagrammatic view of one embodiment of a medical navigation and visualization system.

Referring now to the drawings wherein like reference numerals are used to identify identical components in the various views, FIG. 1 illustrates one exemplary embodiment of a medical navigation and visualization system 10 (e.g., positioning system) for use in navigating an elongated medical device within a body of a patient and generating images of the device within the body of the patient and/or images of internal cavities (e.g., heart chambers) of a patient. Such a system 10 is also discussed in detail in U.S. Pat. No. 7,263,397, entitled: "METHOD AND APPARATUS FOR CATHETER NAVIGATION AND LOCATION AND MAPPING IN THE HEART," which is assigned to the assignee of this patent application, the entire disclosure of which is incorporated by reference in its entirety herein. In the illustrated embodiment, the system 10 includes, among other components, a mapping system 14 and processor apparatus 16 attached to an elongate medical device 12. In this embodiment, the elongated medical device is a catheter 12. The processing apparatus 16 may take the form of an Electronic Control Unit (ECU), for example, that is configured to generate and render an image of catheter 12, internal patient cavities (e.g., heart 20) and output the images to a display 44. The system 10 may further include a user input device (not shown). Although the system is described in terms of, among other things, rendering images a catheter, it should be understood that various elongate medical devices (e.g., introducer sheaths, pacing leads, etc.) could be rendered using the system.

Figure 2:
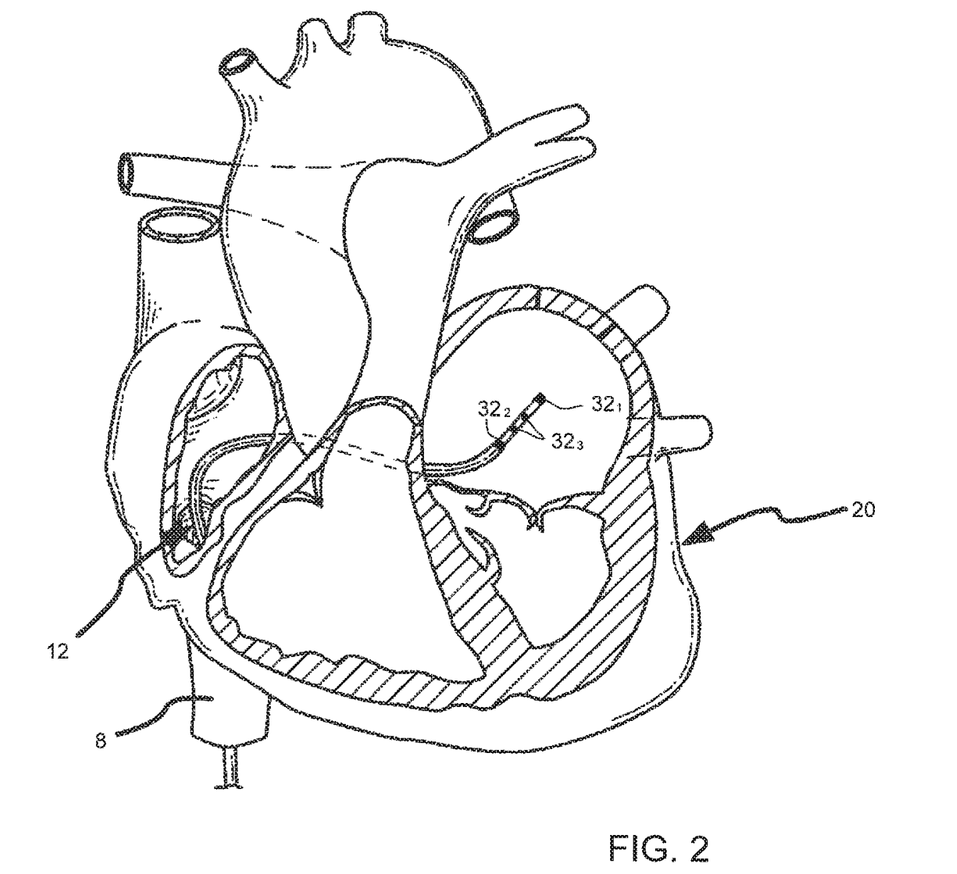
FIG. 2 is a diagrammatic view of a catheter disposed in a patient heart.

As illustrated in FIGS. 1 and 2, the catheter 12 is configured to be inserted into a patient's body 18, and more particularly, into the patient's heart 20. The catheter 12 may include cable connectors, a handle, a proximal shaft and a distal end (not shown). As used herein, "proximal" refers to a direction toward the portion of the catheter 12 near the clinician, and "distal" refers to a direction away from the clinician and (generally) inside the body of a patient. Such a connector provides mechanical, fluid, and electrical connection(s) for cables extending to the ECU and/or other components of system 10 (e.g., a visualization, navigation, and/or mapping system, ablation generator, irrigation source, etc.). The handle, which is disposed at the proximal end of a shaft of the catheter 12, provides a location for the clinician to hold the catheter 12 and may further provide means for steering or guiding the catheter within the body 18 of the patient. The catheter 12 may comprise an electrophysiological (EP) catheter for use in gathering EP data associated with the heart 20 to enable generation of an image of the geometry of the heart surface and related EP data. The catheter 12 may also allow removal of bodily fluids or injection of fluids and medicine into the body and may further provide a means for transporting surgical tools or instruments within a body including those used for pacing or tissue ablation. Although the catheter 12 is described as an EP catheter in an embodiment, it should be understood that the system can be used with a variety of different types of catheters including, for example, intracardiac echocardiography (ICE) catheters and ablation catheters using a wide variety of ablative energies (e.g., radiofrequency, cryogenic, ultrasound, laser or other light, etc.).

As shown in FIG. 2, the catheter 12 may include a plurality of electrodes 32 such as distal tip electrode 321, proximal ring electrode 322, and intermediate ring electrodes 323 (hereafter '32' unless specifically referenced). The electrodes 32 are provided to generate information regarding the position of catheter 12 and therefore may function as position sensors. The electrodes 32 also provide information regarding the geometry of the heart 20. In this regard, the electrodes may be referred to as "mapping electrodes." In various embodiments, the catheter 12 may also include one or more magnetic position sensors (not shown). The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads. As illustrated, cardiac access may be provided by inserting an introducer or sheath 8 in the femoral vein in the right leg. The sheath is then maneuvered up to the inferior vena cava and into the right atrium to provide access for the catheter 12 into the heart. The sheath and/or a catheter extending through the sheath may pass through an interatrial septum between the right atrium and left atrium to provides access to the left atrium as well as the pulmonary veins. Other cardiac access routes are possible.

Referring again to FIG. 1, the system further includes a plurality of surface or patch electrodes 38, a multiplex switch 40, and a signal generator 42 (e.g., frequency source). Other components are possible. The processing apparatus 16 may include a programmable microprocessor, microcontroller, CPU, or may include an application specific integrated circuit (ASIC). Further, the processing apparatus 16 may include a memory 22 and an input/output (I/O) interface through which the processing apparatus 16 may receive a plurality of input signals including, for example, signals generated by patch electrodes $38_{X1}$, $38_{X2}$; $38_{Y1}$, $38_{Y2}$; $38_{Z1}$, $38_{Z2}$ and $38_B$ (hereafter 38 unless specifically referenced) and the catheter electrodes. Further the processing apparatus may generate a plurality of output signals including, for example, those used to control and/or provide data to, for example, display device 44 and switch 40. The processing apparatus 16 may be configured to perform various functions, such as those described in greater detail below, with appropriate programming instructions or code (i.e., software). Accordingly, the processing apparatus 16 is programmed with one or more computer programs encoded on a computer storage medium for performing the functionality described herein.

With the exception of a reference patch electrode $38_B$ called a "belly patch electrode," the patch electrodes 38 are provided to generate electrical signals used, for example, in determining the position and orientation of the catheter 12 within a three-dimensional coordinate system (e.g., three-dimensional space). In one embodiment, the patch electrodes 38 are placed orthogonally on the surface of the body 18 and are used to create axes-specific electric fields within body 18. For instance, in one embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. Though discussed with respect to an orthogonal arrangement of patch electrodes 38, the present disclosure is not meant to be so limited. Rather, in other embodiments, non-orthogonal arrangements (e.g., arrangements of non-orthogonal dipoles) may be utilized to determine the location coordinates (e.g., positions) of the electrodes 32. In addition, a reference electrode (e.g., $38_B$) is attached to the patient body 18. Each of patch electrodes 38 may be coupled to multiplex switch 40. In this embodiment, the processing apparatus 16 is configured, through appropriate software, to provide control signals to the switch 40 to thereby sequentially couple pairs of electrodes 38 to the signal generator 42, which applies drive signals to the pairs of electrodes. Excitation of each pair of electrodes 38 generates an electric field within the body 18 and within an area of interest such as the heart 20. Voltage levels at non-excited electrodes 38, which are referenced to the belly patch electrode $38_B$, are filtered and converted and provided to the processing apparatus 16 for use as reference values. The belly patch electrode $38_B$ is seen in the figure is an alternative to a fixed intra-cardiac electrode, which may be utilized in alternate embodiments. That is, in many instances, a coronary sinus electrode or other fixed electrode in the heart 20 can be used as a reference for measuring voltages and displacements.

Electrodes 32 on the catheter 12 are disposed within electrical fields created in a three-dimension space (e.g., within the heart 20) by exciting the patch electrodes 38. These electrodes 32 experience voltages that are dependent on the location between the patch electrodes 38 and the position of the electrodes 32 relative to the surface of the heart 20. Voltage measurement comparisons (e.g., impedance responses) can be used to determine the position of the electrodes 32 within the heart 20. Movement of the electrodes 32 within the heart 20 (e.g., within a heart chamber) produces information regarding the geometry of the heart 20, EP data as well as location information for the catheter. All of the raw patch voltage data is measured by the A-to-D converter 26 and stored in the processing system/ECU 16 under the direction of software. A filter 27 may subsequently filter the data to remove electronic noise and cardiac motion artifact.

The electrode excitation process occurs rapidly and sequentially as alternate sets of patch electrodes 38 are selected, and the remaining members of the set are used to measure voltages. This collection of voltage measurements may be referred to herein as the "patch data set". The software has access to each individual voltage measurement made at each individual patch electrode 38 during each excitation of each pair of electrodes $38_{X1}$, $38_{X2}$; $38_{Y1}$, $38_{Y2}$; and $38_{Z1}$, $38_{Z2}$. The raw patch data is used to determine the "raw" location in three spaces (X, Y, Z) of the electrodes 32 (e.g., mapping electrodes) inside the heart 20. The patch data set may also be used to create, for example, a respiration compensation value to improve the raw location data for the locations of the electrodes.

Figure 3A:
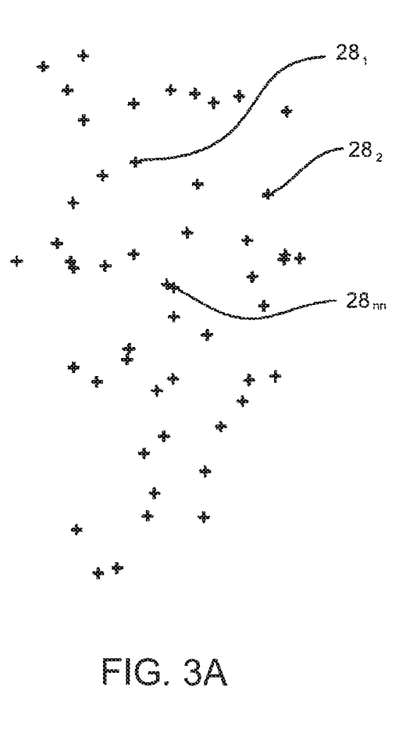
FIG. 3A is a set of data points corresponding to locations of electrodes of a catheter disposed in a patient heart cavity.
Figure 3B:
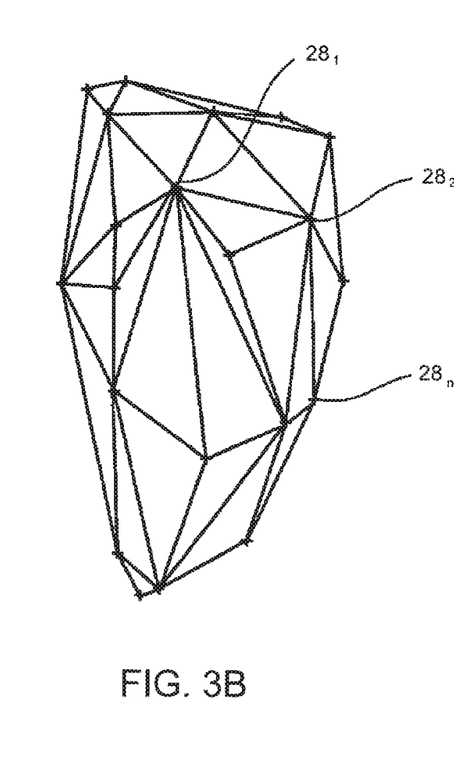
FIG. 3B is an exemplary map of the heart cavity generated from the data points of FIG. 3A.

If the mapping electrodes 32 are swept around in the heart chamber while the heart 20 is beating, a large number of electrode locations are collected. These data points $28_{1-nn}$ (hereafter 28) may be taken at all stages of the heartbeat and without regard to the cardiac phase. See. FIG. 3A. Since the heart 20 changes shape during contraction, only a small number of the points 28 represent the maximum heart volume. By selecting the most exterior points 28, it is possible to create a "shell" 30 or map representing the shape of an interior chamber of the heart 20 as illustrated in a simplified drawing of FIG. 3B, which may be output as an image on the display 44 as illustrated in in of FIG. 1. It will be appreciated that, in use, the shell 30 may be much more detailed and that the shell/map illustrated in FIG. 3B is provided by way of illustration only. The creation of such shells/maps representing internal chamber(s) of a heart is more fully disclosed in U.S. Pat. No. 7,263,397 as incorporated above.

The system 10 determines the position and orientation of the electrodes 32 on an elongate medical device such as the catheter 12. In addition to using this information to generate a map of the interior of the heart, the mapping system 14 may also use this position and orientation data to generate an image of the catheter 12 within the heart 20. More particularly, the processing apparatus 16 and the mapping system 14 is configured to acquire measured data points (e.g., impedance responses) collected using the electrodes 32, where the measured data points corresponding to respective positions of electrodes 32. Using various known algorithms, the processing apparatus 16 may then determine the location (position and orientation) of each electrode 32 and record it as a measured data point corresponding to a respective position of each sensor in a memory or storage device, such as a memory 22, associated with or accessible by the processing apparatus 16. These data points may then be utilized by the model construction system to generate a map of an interior patient cavity (e.g., heart chamber) and/or to generate an image of the catheter. In the latter regard, mapping system 14 acquires the measured data points by activating electrodes 32 as described above. In an embodiment, the model construction system 14 is configured to describe the measured data points as deviations from a parametric form (e.g., a curve, in the case of a one-dimensional catheter 12, or a plane, in the case of a two-dimensional catheter 12) and generate an image of the catheter using such deviations. Stated otherwise, the mapping system or a separate modeling system (not shown) utilizes the measured data points with a mathematical model that describes a particular catheter supporting the electrodes to generate an image of that catheter based on the positions of the data points. One exemplary model construction system is set forth in U.S. Pat. Pub No. 2018/0014751 entitled "Methods and Systems for Generating Smoothed Images of an Elongate Medical Device" the entire disclosure of which is incorporated herein by reference.

Figure 4A:
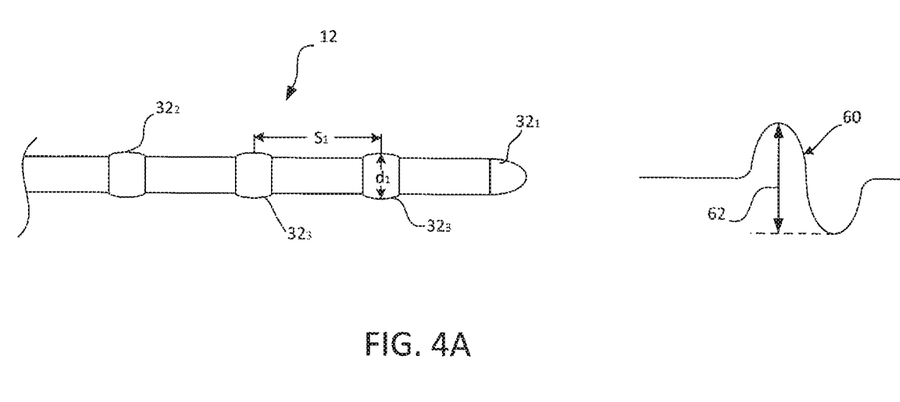
FIGS. 4A and 4B are diagrammatic depictions of two differently configured catheter and their responses to common signal.

FIGS. 2 and 4A illustrate the catheter 12, which may be a high-density mapping catheter, as disposed in the heart 10. As noted, the catheter 12 has a tip electrode $32_1$ a proximal ring electrode $32_2$, and one or more intermediate ring electrodes $32_3$, $32_4$ (hereafter 32 unless specifically referenced). When these electrodes 32 lie in the heart 20 (See FIG. 2), the location process detects their location in the heart 10. Further, when the electrodes 32 lie on the surface of the heart, each such electrode 32 can be used to measure the voltage on the heart surface. The magnitude of this voltage, as well as the timing relationship of the signal with respect to the heartbeat events, may be measured and presented to, for example, a cardiologist through the display 44. That is, a catheter may be used to perform an electrophysiology study to record electrical signals within or from cardiac cavities. By way of example, a peak-to-peak voltage (e.g., signal amplitude) measured at a particular location on the heart wall is capable of showing areas of diminished or otherwise altered conductivity, which may reflect, for example, an infarcted region of heart tissue. This information may be utilized to direct therapy (e.g., ablation) to desired regions within the heart.

When performing an electrophysiology study to record electrical signals from cardiac cavities, a physician or other technician typically utilizes a dedicated catheter or 'diagnostic catheter' having known technical specifications or characteristics that influence the recorded electrical signals. Such known characteristics may include, without limitation, electrode size, electrode shape, electrode material and/or electrode spacing. In use, the same catheter that is used for mapping an interior of a cardiac cavity may also be used to determine regions in the heart that are infarcted, sources of arrhythmia and/or atrial fibrillation, to name a few. Such electrophysiological information may be incorporated into or projected onto the map of the cardiac cavity for subsequent use in directing therapy to such identified/affected regions.

Commonly, therapy is applied to the affected region(s) using a separate therapeutic catheter having a configuration that is different than the diagnostic catheter. That is, physicians use a therapeutic catheter (e.g., ablation catheter) to apply therapy to affected regions after the cardiac cavity is mapped using a diagnostic catheter. In such an arrangement, a physician maps the cardiac cavity using the diagnostic catheter and then removes the diagnostic catheter once the mapping is complete. The physician then routes the therapeutic catheter into the heart. Therapy may then be applied using the previously generated map as a guide. If additional mapping is required, the physician will remove the therapeutic catheter and reinsert the diagnostic catheter. That is, to maintain a consistent map throughout the duration of the study, additional mapping typically requires use of the same diagnostic catheter that performed the original mapping. However, in a number of instances, it may be desirable to map on-the-fly using the catheter currently within the cardiac cavity (e.g., therapeutic catheter). By way of example, specific cardiac rhythms may appear during therapy and need to be mapped quickly before they disappear. In such an instance, a physician may not have time to change catheters. Accordingly, it would be desirable to utilize a current catheter (e.g., therapeutic catheter) to add to the existing map generated by a previous catheter (e.g., diagnostic catheter) even if the current and previous catheters have different configurations. That is, it would be desirable to merge the data from a current catheter with the data from the diagnostic catheter to update a map of a cardiac cavity.

Figure 4B:
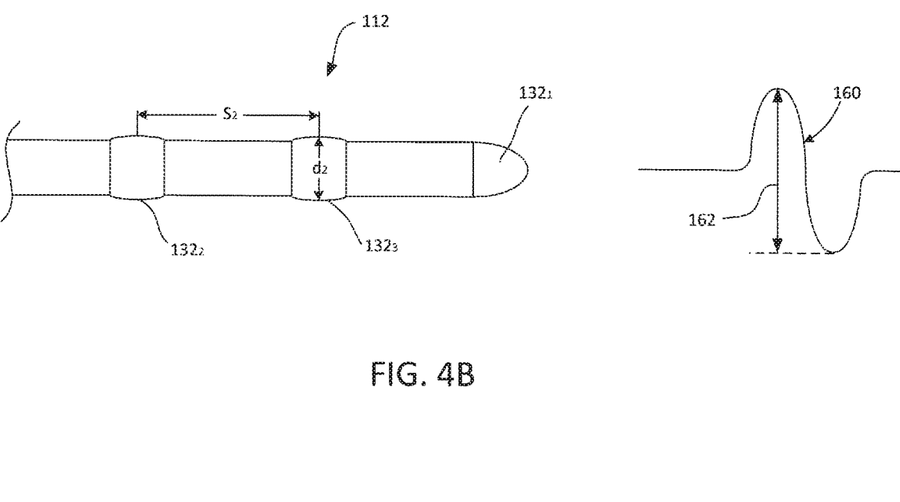

As previously noted, technical specifications (e.g., physical characteristics) of catheters influence recorded electrical signals/responses. That is, differently configured catheters (e.g., different electrode sizes, shapes, materials, spacings, etc.) may record responses from electrodes having different peak-to-peak voltages (e.g., signal amplitudes) even if these responses are measured at the same location and/or point in a cardiac cavity. FIGS. 4A and 4B show an exemplary mapping or diagnostic catheter 12 and an exemplary therapeutic catheter 112 (e.g., ablation catheter). As illustrated, the exemplary diagnostic/mapping catheter 12 has electrodes with a diameter '$d_1$' of 2 mm and an inter-electrode spacing '$S_1$' of 5 mm while the exemplary therapeutic catheter 112 has electrodes with a diameter '$d_2$' of 3 mm and an inter-electrode spacing '$S_2$' of 7 mm. FIGS. 4A and 4B also show exemplary signal traces/responses 60, 160 of sampled electrodes of the catheters 12, 112 when disposed in a homogeneous medium (e.g., saline tank), as detected between, for example, a tip electrode and a first ring electrode. As shown, the response 60 of the diagnostic catheter between the electrodes (e.g., $32_1$ and $32_3$) of the diagnostic catheter 12 differs from the response 160 between the electrodes (e.g., $132_1$ and $132_3$) of the therapeutic catheter 132 when the responses are measured under identical conditions and identical locations. As shown, the amplitudes 62, 162 (e.g., peak-to-peak voltages) of the responses 60, 160 may differ significantly (e.g., 62≠162). In such a situation, use of signals or responses recorded from a therapeutic catheter 112 to update a map generated by a differently configured diagnostic catheter 12 may result in distortions to an updated map.

To allow merging of data from differently configured catheters in a common map, the present disclosure applies a corrective coefficient or transfer function to the recorded electrical signals of one or both catheters to counter-balance variable influences of catheter specific characteristics on recorded signals. That is, the recorded responses may be normalized such that signals from differently configured catheters can be merged in or on a common map with little or no distortion. Stated otherwise, the recorded responses of one or both catheters may be scaled such that parameters (e.g., amplitudes) of these responses are in a common frame of reference. Such scaling permits use of responses from differently configured catheters on a common map.

In a first embodiment, the corrective coefficient or transfer function may be represented as a single dedicated magnifier value associated with each catheter. Such a magnifier represents a multiplication factor, which is always greater than zero, by which the electrical signal/response of a specific catheter is multiplied (e.g., adjusted) during signal acquisition and/or recording such that an amplitude of a recorded signal/response of a first catheter may be normalized to recorded signals/responses of another catheter. In an embodiment, the magnifier may be referenced to a reference catheter, which may be a real catheter (e.g., diagnostic catheter) or a theoretical catheter. In such an arrangement, multiple catheters may be tested in identical situations (e.g., saline tank) to identify, for example, the amplitude of a response for a common location in a common media to a common drive signal(s) (e.g., applied by surface patch electrodes).

Figure 5:
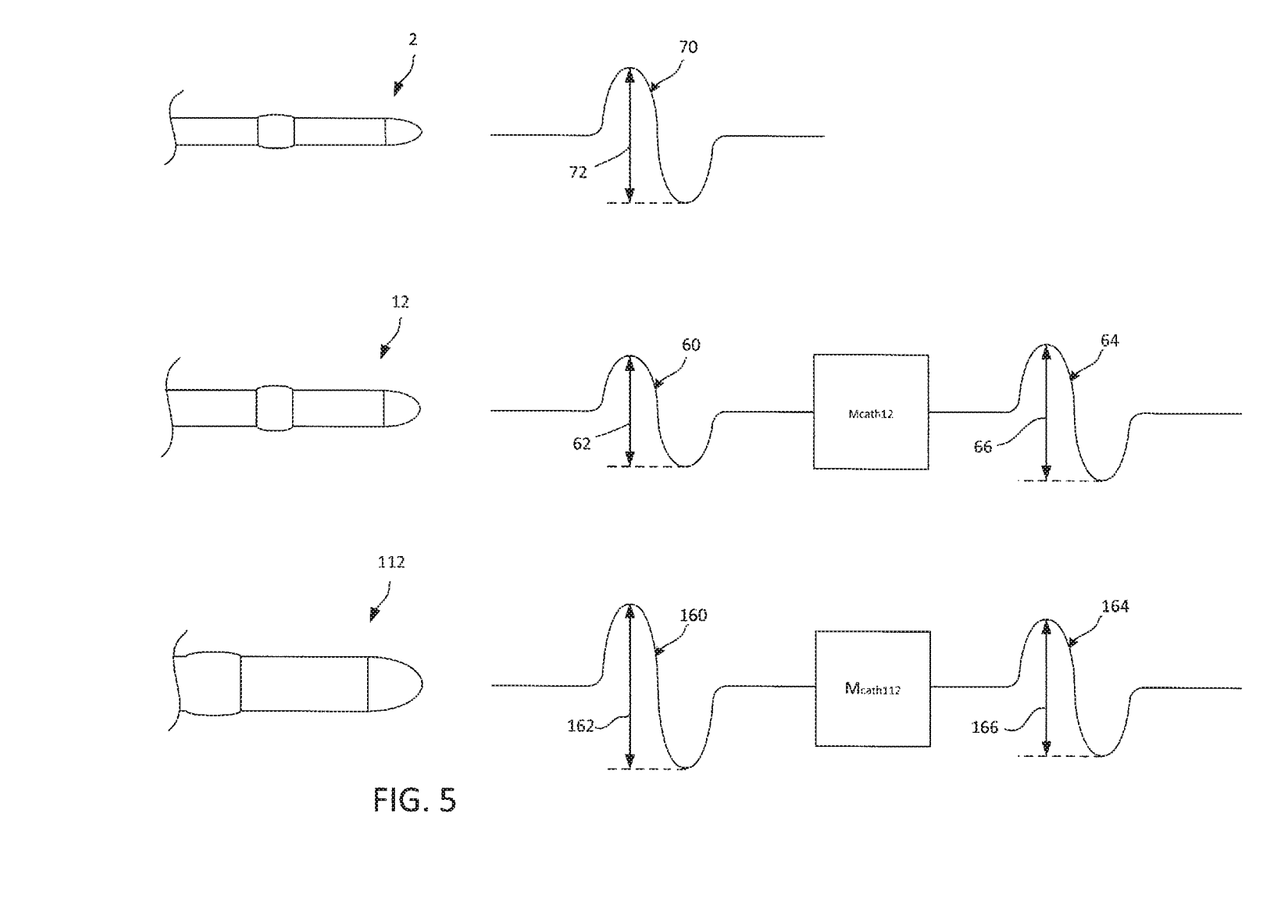
FIG. 5 is a diagrammatic depiction of two embodiments of catheters and their responses to an applied signal relative to a reference catheter and is response to the applied signal.

FIG. 5 illustrates an embodiment where a reference catheter 2, a diagnostic catheter 12 and a therapeutic catheter 112 are tested under identical conditions. The response 70 of the reference catheter 2 is subsequently utilized to define a magnifier for each of the other catheters 12, 112. More specifically, the relative ratio of the magnitude/amplitude (e.g., 62 and 162) of the response 60, 160 of each catheter (e.g., 12 and 112) relative to the magnitude/amplitude 72 of the reference catheter response 70 defines the magnifier for each catheter. Specifically:

$$M_{Cath(x)} = \frac{A_{ref}}{A_{Cath(x)}} \qquad \text{Eq. (1)}$$

Where $A_{ref}$ is the amplitude (e.g., 72) measured by the reference catheter 2 and $A_{Cath(x)}$ is the amplitude (e.g., 62 or 162) measured by a specific catheter (e.g., 12 or 112). Once the multiplier is defined for each catheter (e.g., 12 and 112), the multiplier may be used to adjust the magnitude/amplitude of any responses measured or recorded by the catheters according to the following equation:

$$A_{cor(x)} = M_{Cath(x)} A_{Cath(x)} \qquad \text{Eq. (2)}$$

Where $A_{cor(x)}$ represents an adjusted amplitude of a response of a specific catheter (x) to a signal that is adjusted to substantially match an amplitude of a response of another catheter (e.g., reference catheter) to the same signal.

As illustrated in FIG. 5, application of each catheter specific magnifier $M_{cath(x)}$ to the responses 60, 160 of the two catheters 12, 112, respectively, adjusts the amplitudes 62, 162 of those responses to adjusted amplitudes 66, 166 having the same amplitude 72 as the response 70 of the reference catheter 2. By way of example, where the response 70 of the reference catheter 2 has an exemplary unitless amplitude (e.g., 72) of ten (10) and the response 60 of the diagnostic catheter 12 has an exemplary unitless amplitude 62 of eight (8), an amplitude 66 of an adjusted response 64 of the diagnostic catheter 12 will be ten (10). In such an arrangement, a magnifier (e.g., $M_{Cath12}$) for the diagnostic catheter 12 will be 1.25 (e.g., 10/8). Following the same example, a magnifier (e.g., $M_{cathm}$) for the therapeutic catheter 112 having an exemplary unitless amplitude 162 of twelve (12) will be 0.833 (e.g., 10/12) resulting in an adjusted amplitude 166 of the adjusted response 164 of the therapeutic catheter 112 also being ten (10). Such magnifiers may be generated for multiple catheters (e.g., commercially available catheters) and may be stored, for example, within a database in the memory 22 of the ECU where they are accessible by the processing apparatus 16. See FIG. 1.

During a procedure, a physician or other technician may identify the specific catheters used for diagnostic and/or therapeutic purposes. In such an arrangement, the ECU and/or processor 16 may access catheter specific magnifiers from the memory 22 such that the amplitude of an acquired signal/response may be modified prior to generating a data point (e.g., mapped point) or otherwise processing the response. Of further note, the system 10 may utilize information associated with two catheters to normalize responses of a second catheter directly to a first catheter based on the magnifiers of the first and second catheter. That is, rather than normalizing responses of, for example, both a diagnostic catheter 12 and a therapeutic catheter 112 to a reference catheter 2, responses of the therapeutic catheter 112 may be normalized directly to responses of the diagnostic catheter 12. In such an embodiment, responses of the diagnostic catheter (e.g., first catheter) is not modified while the amplitude of a therapeutic catheter (e.g., second catheter) is modified using the ratio between the magnifier of the first and second catheters as follows:

$$A_{Cor2} = \frac{M_{cath1}}{M_{Cath2}} \cdot A_{Cath2} \qquad \text{Eq. (3)}$$

Where $A_{cath2}$ is the Amplitude of a signal from the second catheter, $M_{cath1}$ is a magnifier value of the first catheter, $M_{cath2}$ is the magnifier value of the second catheter and $A_{Cor2}$ is the corrected amplitude for the second catheter. In this embodiment, an amplitude of a signal of a second catheter may be adjusted directly to the amplitude of a first catheter. If multiple catheters (e.g., three or more) are used during a procedure, normalization is most commonly to a reference/theoretical catheter. In any embodiment, the magnifier allows for adjusting responses to a common frame of reference such that data from two or more differently configured catheters may be merged into or onto a common map without distortion.

In another embodiment, a corrective coefficient or transfer function may represent multiple catheter characteristics that influence signal amplitude. In such an embodiment, ratios of characteristics (e.g., electrode shape, size, spacing material, etc.) of a reference catheter and corresponding characteristics of a selected catheter (e.g., normalized catheter) may be established. In such an arrangement, the ratios of the characteristics and their effect on the change in signal amplitude may be evaluated to define a magnifier that is a product of multiple characteristics. By way of example, a reference catheter may have an electrode size of 2 mm and an inter-electrode spacing of 5 mm while a selected catheter that will be normalized to the reference catheter may have an electrode size of 3 mm and an inter-electrode spacing of 7 mm. In such an example, a magnifier may be defined based on these two characteristics. That is, characteristic 'C1' may represent electrode size and characteristic two 'C2' may represent electrode spacing. A magnifier may be defined as follows:

$$M_{Cath(x)} = a \frac{c1_{ref}}{c1_{Cath(x)}} b \frac{c1_{ref}}{c1_{Cath(x)}} \qquad \text{Eq. (4)}$$

Where $M_{cath(x)}$ is the product of the two ratios of the two characteristics for the reference catheter and the selected catheter. Further, each ratio may, but need not, be multiplied by a predetermined constant (e.g., a and b) to account for the influence of each characteristic on measured signal amplitude. For example, the influence of each characteristic may be empirically determined during testing. Further, it will be appreciated that additional characteristics (e.g., electrode material, shape etc.) and the influence of these characteristics on measured signal amplitudes may be defined. Once defined, the magnifier may be used to adjust or normalize the amplitude of the catheter in accordance with Equations 2 or 3 as set forth above.

Figure 6:
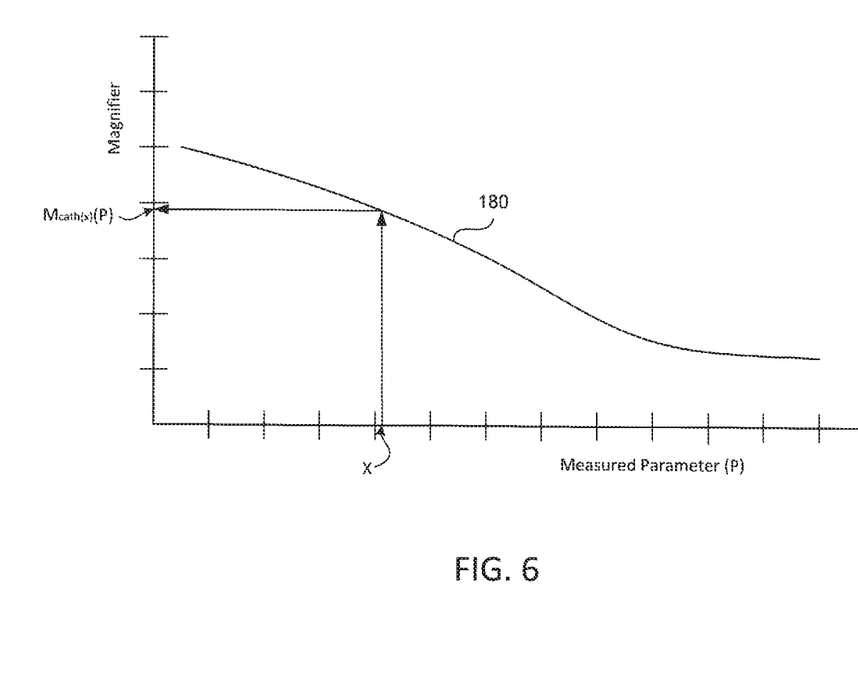
FIG. 6 is an exemplary depiction of a transfer function for a specific parameter between a refence catheter and a selected catheter.

In another embodiment, adjustment of an amplitude for a selected catheter may be based on a magnifier that is a function of a specific parameter measured or otherwise available during an electrophysiological study. Such specific parameters may include, for example, contact force and impedance. Further, in the case of these specific parameters, a transfer function may be further defined based on tissue type (e.g., atrial, mitral etc.). FIG. 6 graphically illustrates a transfer function 180 (e.g., curve) generated for a specific parameter (P) that is measured during an electrophysiological study. The transfer function is defined between a reference catheter and a selected catheter for the specific parameter (e.g., $Cath_{(x)}(P)$) in laboratory testing. Use of such a curve as a transfer function allows for the identification of a non-linear magnifier values. By way of example, the transfer function 180 may represent a contact force value (i.e., specific parameter P) between an electrode and cardiac tissue. In such an arrangement, a range of contact forces are applied to both an electrode (e.g. tip electrode) the reference catheter and a corresponding electrode (e.g., tip electrode) of the selected catheter to generate a curve or transfer function 180 that correlates the force values generated by the tip electrode of the selected catheter to the force values generated by the tip electrode of the reference catheter. This allows determining a magnifier value $MCath_{(x)}(P)$ (i.e., vertical axis) that translates a force value generated by the selected catheter to a corresponding force value generated by the reference catheter for a common contact condition. That is, a measured force value 'X' output by the selected catheter during an electrophysiological study can be used to select a magnifier to translate this force value 'X' to force value that would be generated by the reference catheter. While discussed in terms of contact force, it will be appreciated that the same may be done for any of a variety of specified parameters. When utilizing such information to adjust an amplitude of a measured response by a selected catheter for a specific parameter (P) to the reference catheter, the following equation may be used:

$$A_{cor(x)} = M_{Cath(x)}(P) A_{Cath(x)} \qquad \text{Eq. (5)}$$

Likewise, a similar equation may be used to normalize amplitudes of a specific parameter responses of a second catheter directly to a first catheter based on the magnifiers of the first and second catheter to a reference catheter. Specifically:

$$A_{Cor2} = \frac{M_{cath1}(P)}{M_{Cath2}(P)} \cdot A_{Cath2} \qquad \text{Eq. (6)}$$

Where $A_{cath2}$ is the Amplitude of a signal from the second catheter, $M_{cath1}(P)$ is a magnifier value of the first catheter to a reference catheter for the specified parameter, $M_{cath2}(P)$ is the magnifier value of the second catheter to the reference catheter for the specified parameter and $A_{cor2}$ is the corrected amplitude for the second catheter. In this arrangement, the first and second catheters may be normalized to the common reference catheter for a specific parameter. As above, the transfer function for each of a plurality of catheters may be stored within a database in the memory of the ECU where they are accessible by the processing apparatus.

Figure 7:
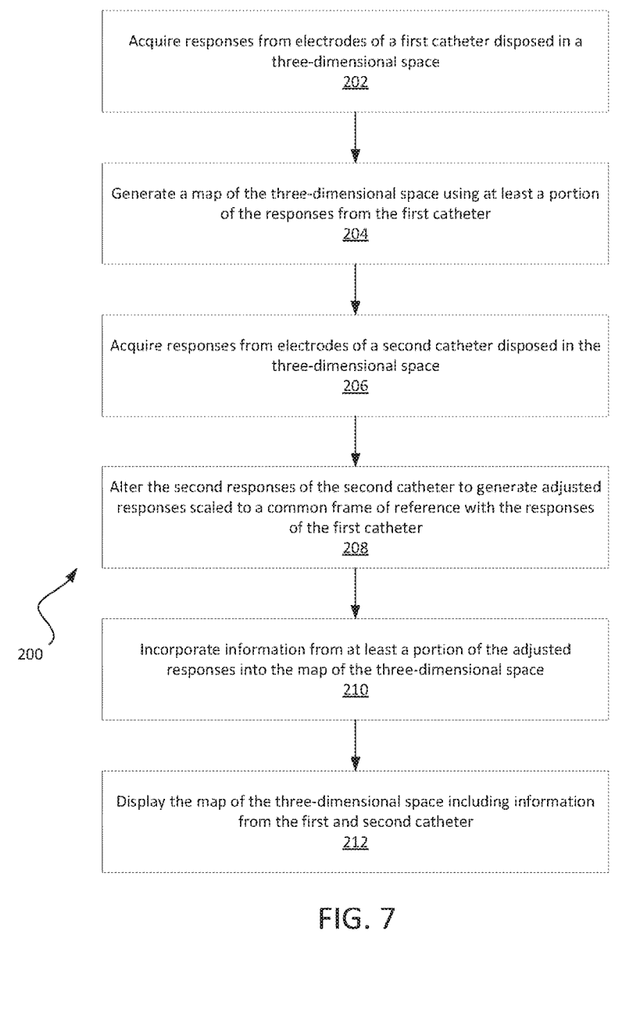
FIG. 7 illustrates one exemplary process flow sheet for normalizing responses between differently configured catheters to merge data on a common map.

FIG. 7 illustrates one process 200 for merging data from differently configured catheters into or onto a common map. The process includes acquiring 202 electrode responses (e.g., at the ECU) from electrodes of a first catheter disposed in a three-dimensional space, such as a heart cavity. As per the prior discussion, the first catheter has first configuration which may include, among other things, specified catheter electrode sizes, spacings and or materials. In an embodiment, information from the responses corresponds to location data points $28_1$-$28_{nn}$ (each illustrated as '+') representing the locations of the electrodes of the catheter. See FIG. 8A. In an embodiment, the location data points generated from the responses of the first catheter may be, for example, plotted to generate 204 a map of the three-dimensional space. For instance, a shell or map 30 may be generated utilizing the responses from the first catheter. See e.g., FIG. 3B. Once a three-dimensional space is initially mapped, second catheter may be inserted into the three-dimensional space. The second catheter may have a specified configuration (e.g., electrode size, spacing material etc.) that is different from the first catheter. The process further includes acquiring 206 responses $128_1$-$128_{nn}$ (each illustrated as '○') from the electrodes of the second catheter, after it is disposed in the three-dimensional space. After acquisition, the second responses of the second catheter may be adjusted or altered 208 to scale these responses to a common frame of reference with the first catheter. That is, a transfer function or magnifier may be applied to the catheter responses of the second catheter to scale these responses to the same frame of reference as responses of the first catheter. This frame of reference may be the frame of reference of the first catheter or the frame of reference of a reference catheter. This is graphically illustrated in FIG. 8A. As shown, the second catheter electrode location responses $128_1$-$128_{nn}$ may initially lie outside of the field of data points generated by the first catheter and would therefore lie outside of the shell or map 30 generated by the first catheter. Accordingly, direct inclusion of this information in the map would result in a distortion of the map. The adjustment 208 of the second catheter electrode responses $128_1$-$128_{nn}$ (e.g., application of the transfer coefficient/multiplier) generates scaled or adjusted responses $130_1$-$130_{nn}$ with the same frame of reference as the responses $28_1$-$28_{nn}$ acquired by the first catheter. As shown, these adjusted responses or adjusted data points $130_1$-$130_{nn}$ fit within the data set of the first catheter. Accordingly, once altered, the adjusted responses $130_1$-$130_{nn}$ (e.g., location data points) from the second catheter may be plotted or otherwise incorporated onto or into an updated map 150 of the three-dimensional space initially generated by the first catheter as shown in FIG. 8B. This is the updated map 150 is a merged map including information from the first catheter as well as information from the second catheter in a common frame of reference and free of distortion.

Figure 8A:
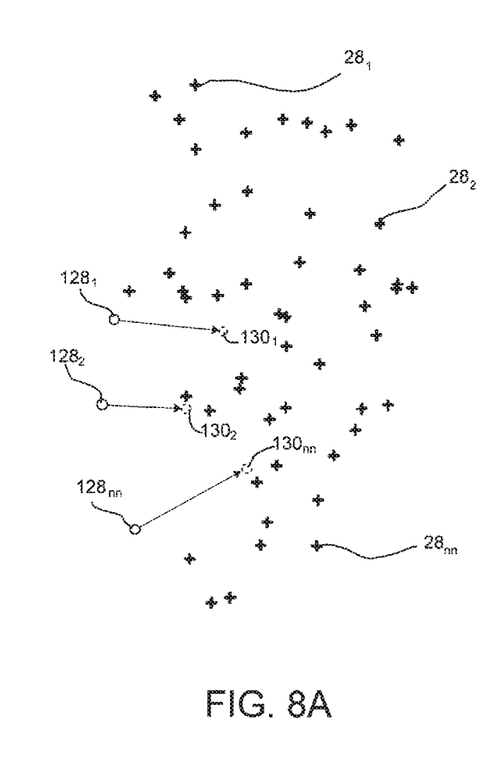
FIG. 8A illustrates location data points collected by differently configured catheters.
Figure 8B:
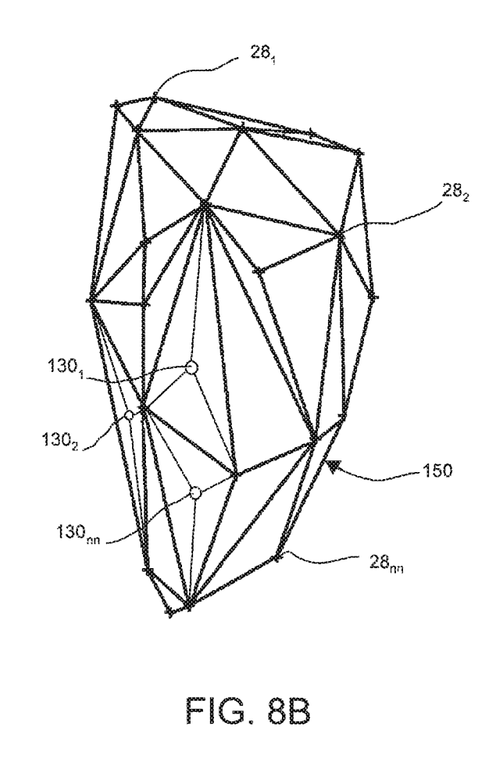
FIG. 8B illustrates the merging of location data points collected by different catheters on a common map.

Though discussed in FIGS. 7, 8A and 8B as utilizing electrode location information, it will be appreciated that additional or different information may be utilized. For instance, impedance and/or contact force may be plotted on the map. That is, the map may identify one or more specific parameters. Further, the first catheter may provide a physical map of the heart cavity while information from the second catheter may provide different information (e.g., contact force) so long as this different information is scaled to a common frame of reference as the information from the first catheter.

All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for use in a medical navigation and visualization system for merging mapping data acquired from different catheters, comprising:
    acquiring first responses from electrodes of a first catheter having a first configuration while the first catheter is disposed within a three-dimensional space;
    generating a map of the three-dimensional space using information from at least a portion of the first responses from the first catheter;
    acquiring second responses from electrodes of a second catheter having a second configuration while the second catheter is disposed within the three-dimensional space, wherein the second configuration of the second catheter is different than the first configuration of the first catheter;
    selecting a predetermined magnifier based on the first configuration of the first catheter and the second configuration of the second catheter, wherein the predetermined magnifier is defined as a ratio of a first common response generated by the first configuration and a second common response generated by the second configuration in response to a common signal under common conditions;
    adjusting the second responses to generate adjusted second responses by multiplying the second responses of the second catheter by the magnifier to scale the second responses to a common frame of reference with the first responses;
    incorporating information from at least a portion of the adjusted second responses into the map of the three-dimensional space to generate an updated map; and
    outputting a display of the updated map to a display device, wherein the updated map includes information from the first catheter and the second catheter.

2. The method of claim 1, wherein the acquiring of the second responses further comprises:
    removing the first catheter from the three-dimensional space after acquiring the first responses; and
    inserting the second catheter into the three-dimensional space after removing the first catheter.

3. The method of claim 1, wherein the magnifier alters amplitudes of the second responses.

4. The method of claim 1, further comprising measuring a parameter during an electrophysiology study performed by the second catheter; and
    selecting the magnifier based on a measured value of the parameter.

5. The method of claim 1, wherein the common frame of reference is a frame of reference of the first catheter.

6. A The method for use in a medical navigation and visualization system for merging mapping data acquired from different catheters, comprising:
    acquiring first responses from electrodes of a first catheter having a first configuration while the first catheter is disposed within a three-dimensional space;
    generating a map of the three-dimensional space using information from at least a portion of the first responses from the first catheter;
    acquiring second responses from electrodes of a second catheter having a second configuration while the second catheter is disposed within the three-dimensional space, wherein the second configuration of the second catheter is different than the first configuration of the first catheter;
    defining-a first ratio of a first physical characteristic of the first catheter to a corresponding first physical characteristic of the second catheter; and
    defining a second ratio of a second physical characteristic of the second catheter to a corresponding second physical characteristic of the first catheter, the a magnifier is a product of the first ratio and the second ratio;
    adjusting the second responses to generate adjusted second responses by multiplying the second responses of the second catheter by the magnifier to scale the second responses to a common frame of reference with the first responses;
    incorporating information from at least a portion of the adjusted second responses into the map of the three-dimensional space to generate an updated map; and
    outputting a display of the updated map to a display device, wherein the updated map includes information from the first catheter and the second catheter.

* * * * *

UNITED STATES PATENT AND TRADEMARK OFFICE
CERTIFICATE OF CORRECTION

PATENT NO. : 11,559,240 B2
APPLICATION NO. : 17/012926
DATED : January 24, 2023
INVENTOR(S) : Cyrille Casset et al.

It is certified that error appears in the above-identified patent and that said Letters Patent is hereby corrected as shown below:

In the Claims

Column 14, Line 36, "characteristic of the first catheter, the a magnifier is" should read -- characteristic of the first catheter, wherein a magnifier is --.

Signed and Sealed this
Eighth Day of August, 2023

Katherine Kelly Vidal
*Director of the United States Patent and Trademark Office*